US006630315B1

United States Patent
Miwa et al.

(10) Patent No.: US 6,630,315 B1
(45) Date of Patent: Oct. 7, 2003

(54) PROCESS FOR PREPARING MAJOR HISTOCOMPATIBILITY ANTIGEN CLASS II PROTEIN AND MATERIALS IN WHICH THE SAME IS BOUND

(75) Inventors: Keishi Miwa, Takatsuki (JP); Mayumi Fukuyama, Kusatsu (JP); Takehiko Uchiyama, Higashimurayama (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 08/929,157

(22) Filed: Sep. 11, 1997

Related U.S. Application Data

(63) Continuation of application No. 08/244,910, filed as application No. PCT/JP93/01480 on Oct. 15, 1993, now abandoned.

(30) Foreign Application Priority Data

| Oct. 15, 1992 | (JP) | 4/277430 |
| Dec. 25, 1992 | (JP) | 4/345915 |
| Dec. 25, 1992 | (JP) | 4/345916 |
| Dec. 25, 1992 | (JP) | 4/345917 |
| Dec. 25, 1992 | (JP) | 4/345918 |

(51) Int. Cl.$^7$ .................. B01D 15/08; C07K 1/22; G01N 33/543; G01N 33/566
(52) U.S. Cl. ............. 435/7.24; 210/679; 210/691; 424/140.1; 435/7.32; 435/7.8; 436/501; 436/5.8; 530/413; 604/5.01; 604/5.02; 604/5.04
(58) Field of Search .............. 435/69.1, 69.3, 435/172.3, 7.24, 7.32, 7.33, 7.8; 530/413; 604/4, 6, 5.01, 5.02, 5.04; 424/140.1; 210/679, 691; 436/501, 518

(56) References Cited

U.S. PATENT DOCUMENTS

| 5,130,297 A | * | 7/1992 | Sharma et al. ............. 514/8 |
| 5,169,941 A | * | 12/1992 | Mach et al. .................. 536/27 |
| 5,260,422 A | * | 11/1993 | Clark et al. ................. 530/403 |
| 5,292,641 A | * | 3/1994 | Pouletty ..................... 435/7.24 |
| 5,583,031 A | * | 12/1996 | Stern ......................... 435/240.2 |

FOREIGN PATENT DOCUMENTS

| EP | 0 432 691 A1 | 6/1991 |
| WO | WO 89/12459 | 12/1989 |
| WO | WO 91/14701 | 10/1991 |
| WO | 92 07952 | * 5/1992 |

OTHER PUBLICATIONS

J. D. Altman et al, Proc. Natl. Acad. Sci. USA, 90, 10330–10334, 1993.*
K. C. Parker et al, Molec. Immunol., 29, 371–378, 1992.*
J. K. Russell et al, Biochem. Biophys. Res. Commun., 168, 696–701, 1990.*
H. M. Johnson et al, Scientific American, Apr. 1992, pp. 92–101.*
Letters to Nature vol. 346, 8/90 pp 474–476 Karp et at The α1 domain of the HLA–DR molecule is essential for high–affinity binding of the toxic shock syndrome toxin–1.

* cited by examiner

*Primary Examiner*—David Saunders
(74) *Attorney, Agent, or Firm*—Nixon & Vanderhye P.C.

(57) ABSTRACT

This invention provides a process for producing major histocompatibility antigen class II protein (hereinafter referred to as "MHC class II" for short) which occurs on the surfaces of antigen-presenting cells and the like, and MHC class II-bound materials in which MHC class II, α and/or β subunit of MHC class II, or a part thereof is bound to a carrier such as beads, fibers and hollow fibers via covalent bond, as well as a module for removing superantigen using the same. This invention also provides a method for detecting or quantifying superantigens using MHC class II or a part thereof having an affinity to the superantigens, as well as an assay kit therefor.

5 Claims, 4 Drawing Sheets

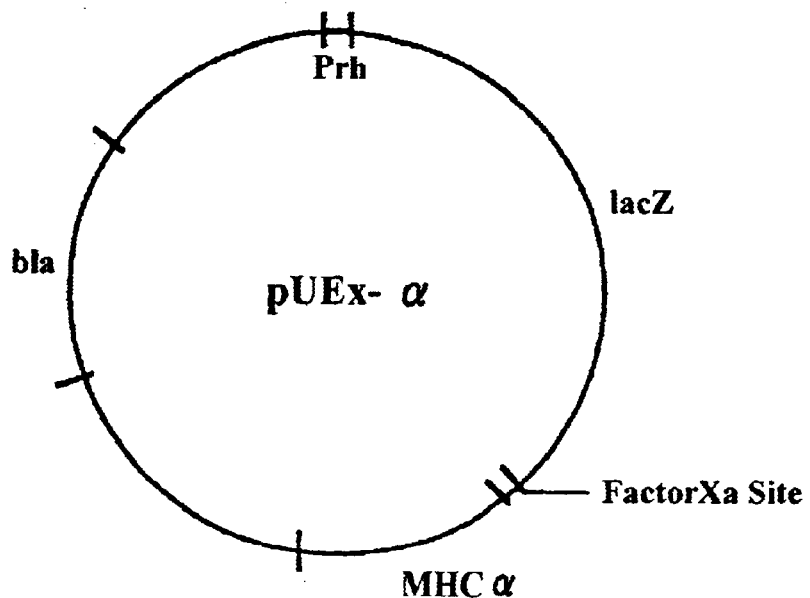

Prh : heat shock promoter
bla : β lactamase gene
lacZ : β galactosidase gene
MHC α : MHC class II α subunit gene
FactorXa site : recognition site of protease Factor Xa Fig. 1  Vector for Expressing α Subunit of MHC Class II

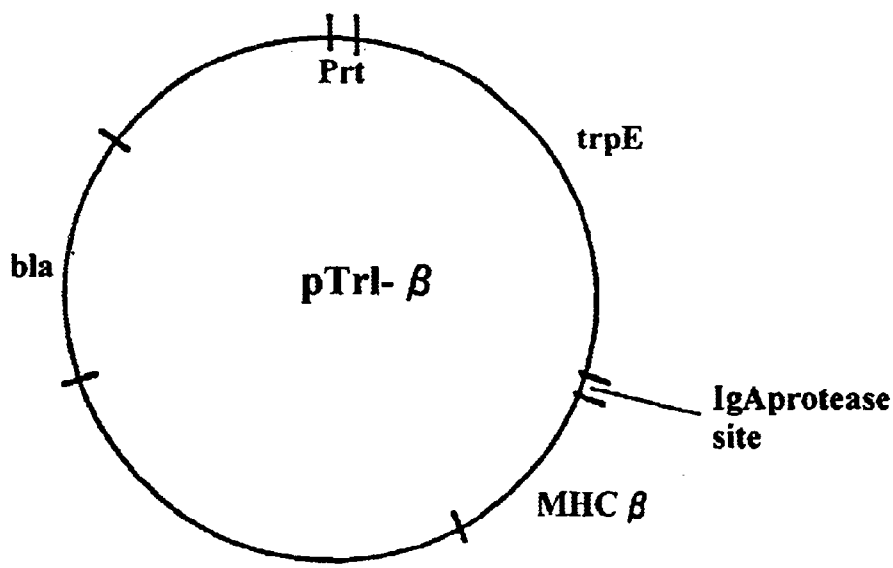

Prt : tryptophan promoter
bla : β lactamase gene
trpE : TrpE protein gene
MHC β : MHC class II β subunit gene
IgAprotease site : recognition site of IgA protease Fig. 2  Vector for Expressing β Subunit of MHC Class II

PROCESS FOR PREPARING MAJOR HISTOCOMPATIBILITY ANTIGEN CLASS II PROTEIN AND MATERIALS IN WHICH THE SAME IS BOUND

This is a continuation of application Ser. No. 08/244,910, filed Jun. 14, 1994, now abandoned which is a 371 of PCT/JP93/01480 filed Oct. 15, 1993.

TECHNICAL FIELD

The present invention relates to a process for producing major histocompatibility antigen class II protein (hereinafter referred to as "MHC class II" for short) occurring on the surface of antigen-presenting cells and the like, and MHC class II-bound materials in which MHC class II, α and/or β subunit of MHC class II, or a part thereof is bound to a carrier such as beads, fibers and hollow fibers via covalent bond, as well as a module for removing superantigens using the same.

This invention also relates to a method for detecting or quantifying superantigens using MHC class II or a part thereof having an affinity to superantigens, as well as an assay kit therefor.

PRIOR ART

MHC class II occurs on the cell surfaces of B cells, macrophages, endothelium cells in blood vessels and the like. MHC class II is a glycoprotein used for distinguishing self from others. Recently, it was found that MHC class II is a binding protein which binds to a group of proteins called superantigens such as toxins of bacteria, and the subtypes of MHC class II in patients suffering from autoimmune diseases are peculiarly distributed, so that it is now regarded as importance in field of medicine and immunology.

Superantigens are a group of proteins which bind to MHC class II on antigen-presenting cells without being processed in the antigen-presenting cells unlike conventional antigens, and form complexes with MHC class II so as to stimulate T cells having a specific V region, thereby abnormally activate immune system.

Superantigens hitherto confirmed include *Staphylococcus aureus* toxin, Streptococcus toxin, Yersinia toxin, some kinds of virus proteins and heat shock proteins. Superantigens may also be identified in the future.

At present, to isolate and obtain MHC class II, it is necessary to introduce MHC class II gene in mammalian cells or insect cells and express the gene, or it is necessary to purify naturally occurring MHC class II from cell membranes of B cells, macrophages, endothelium cells in blood vessels and the like.

However, for obtaining naturally occurring MHC class II from cell membranes in a large scale, a large number of cells are necessary because the amount of MHC class II on the surface of the membranes is small, so that this method takes a long time and a large cost even if cultured cells are employed.

Similarly, for producing recombinant MHC class II by mammalian cells or insect cells by a genetic recombination technique, a large cost and a long time are required for culturing the cells.

Although system for expressing major histocompatibility antigen class I protein by using *Escherichia coli* has been reported (K. C. Parker et al., Molecular Immunology, Vol. 29, 371 (1992)), no such an expression system is known for MHC class II.

Conventional materials to which MHC class II is bound include those in which whole cells expressing MHC class II on the cell surfaces are adsorbed on a plate, and those in which chemically synthesized amino acid sequence that is a part of a subunit of MHC class II is adsorbed on a material (J. K. Russel et al., Biochemical and Biophysical Research Communications, Vol. 168, 696 (1990)).

As for a material for adsorbing superantigens, a material to which antibodies specific to superantigens are immobilized has been reported and the material is used for immunoassays of the superantigens.

The present invention provides a process for producing MHC class II by using bacteria, thereby promoting productivity and ease of operation.

Unlike insect cells and mammalian cells, bacterial cells grow fast, no expensive components such as fetal calf serum and growth factors are necessary to be contained in culture medium, and operations such as subculturing and replacement of culture medium are not necessary.

However, in many cases, proteins originating from mammals are not expressed in bacteria such as *E. coli* because of the problems such as the toxicity to bacteria and the like.

The present inventors studied to improve various expression vectors and succeeded in expressing MHC class II in bacterial cells such as *E. coli*, yeasts and *Bacillus subtilis*, thereby made it possible to produce the protein efficiently in a large scale.

The present invention provides, in the medical field, a blood-purificatlon system for removing pathogenic substances including superantigens, which have affinities to MHC class II, and in the field of immunology, the present invention provides a material capable of binding the pathogenic substances including superantigens, which have affinities to MHC class II, that is used for isolating the pathogenic substances and for immunoassays for assaying the pathogenic substances.

If the whole cells are immobilized on a carrier, since proteins other than MHC class II are also immobilized, the material may have an unknown activity. Further, the freedom of optionally selecting the-density of immobilized MHC class II is limited. As for the material on which a chemically synthesized partial amino acid sequence of the MHC class II subunit is adsorbed, although it can be used for detecting superantigens contained in a high concentration in a buffer, it cannot be used for removing superantigens from the blood because the adsorbed ligand may be liberated from the carrier.

Further, the binding ability of the partial sequence to superantigens is small, so that sufficient performance for detecting and quantifying superantigens cannot be obtained. With the material on which an antibody is immobilized, it is necessary to immobilize different antibodies each of which is specific to each type of superantigens respectively.

DISCLOSURE OF THE INVENTION

The present invention aims at overcoming the above-mentioned problems in the prior art and has the following constitution. That is, the present invention provides (1) A process for producing major histocompatibility antigen class II protein, comprising the step of transforming a microorganism with a gene encoding said major histocompatibility antigen class II protein;

(2) A material in which major histocompatibility antigen class II protein or a part thereof is bound via covalent bond;

(3) A material in which α subunit of major histocompatibility antigen class II protein or a part thereof is bound via covalent bond;
(4) A material in which β subunit of major histocompatibility antigen class II protein or a part thereof is bound via covalent bond;
(5) A module for removing superantigens, comprising said material of any one of (2)–(4);
(6) A method for detecting a superantigen by using major histocompatibility antigen class II protein oria part thereof having a length of not less than 40 amino acid residues, which part has an affinity to said superantigen; and
(7) A method for quantifying a superantigen by using major histocompatibility antigen class II protein or a part thereof having a length of not less than 40 amino acid residues, which part has an affinity to said superantigen.

BRIEF DESCRIPTION OF THE DRAWINGS

FIG. 1 is a schematic view showing an expression vector for expressing MHC class II α subunit gene in *E. coli*.

FIG. 2 is a schematic view showing an expression vector for expressing MHC class II β subunit gene in *E. coli*.

BEST MODE FOR CARRYING OUT THE INVENTION

Figure 3:
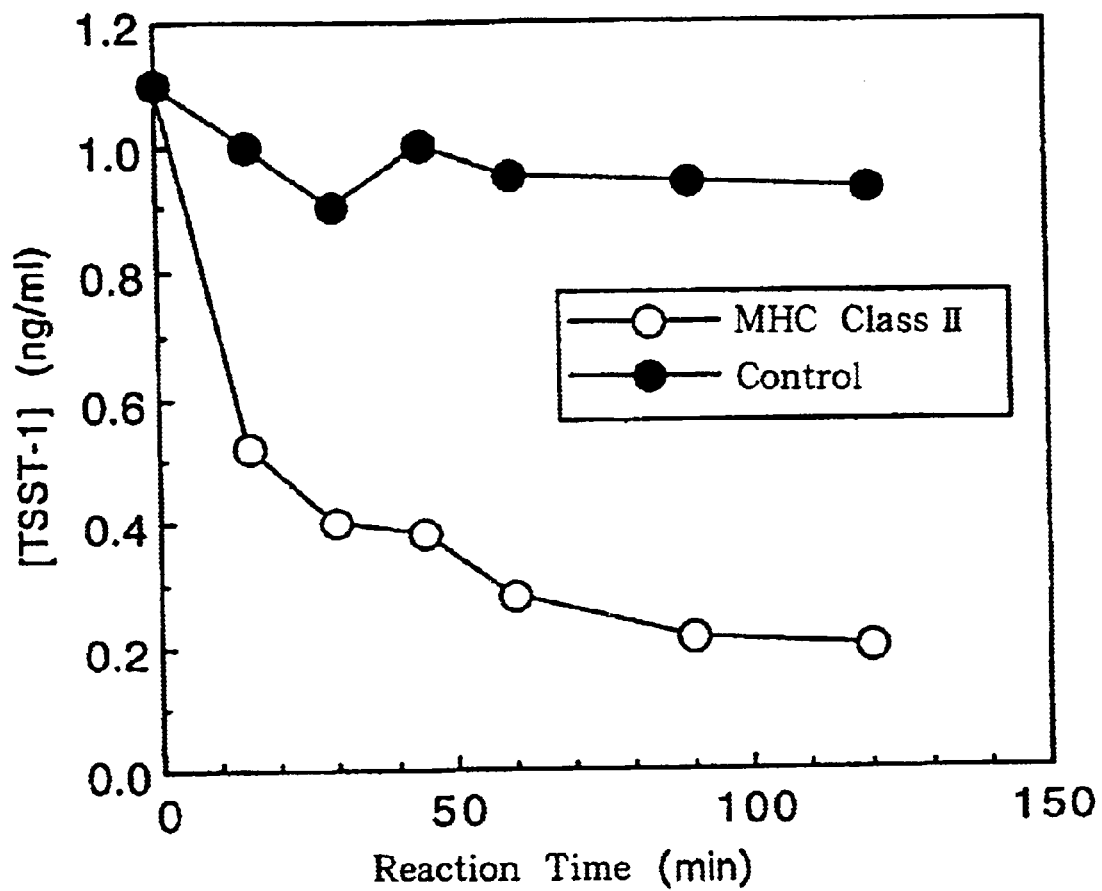
FIG. 3 shows the relationship between the amount of removed TSST-1 from a buffer solution by MHC class II-bound beads and reaction time.
Figure 4:
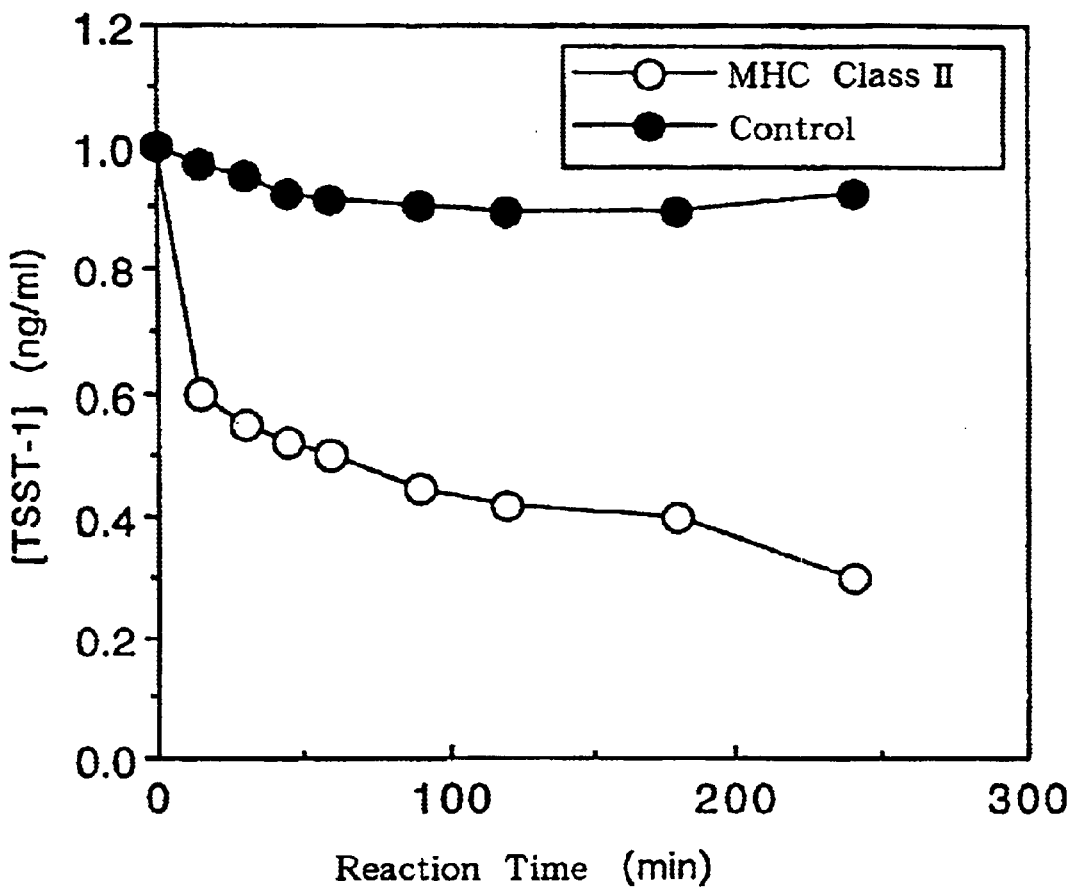
FIG. 4 shows the relationship between the amount of removed TSST-1 from a buffer solution by MHC class II-bound hollow fibers and reaction time.
Figure 5:
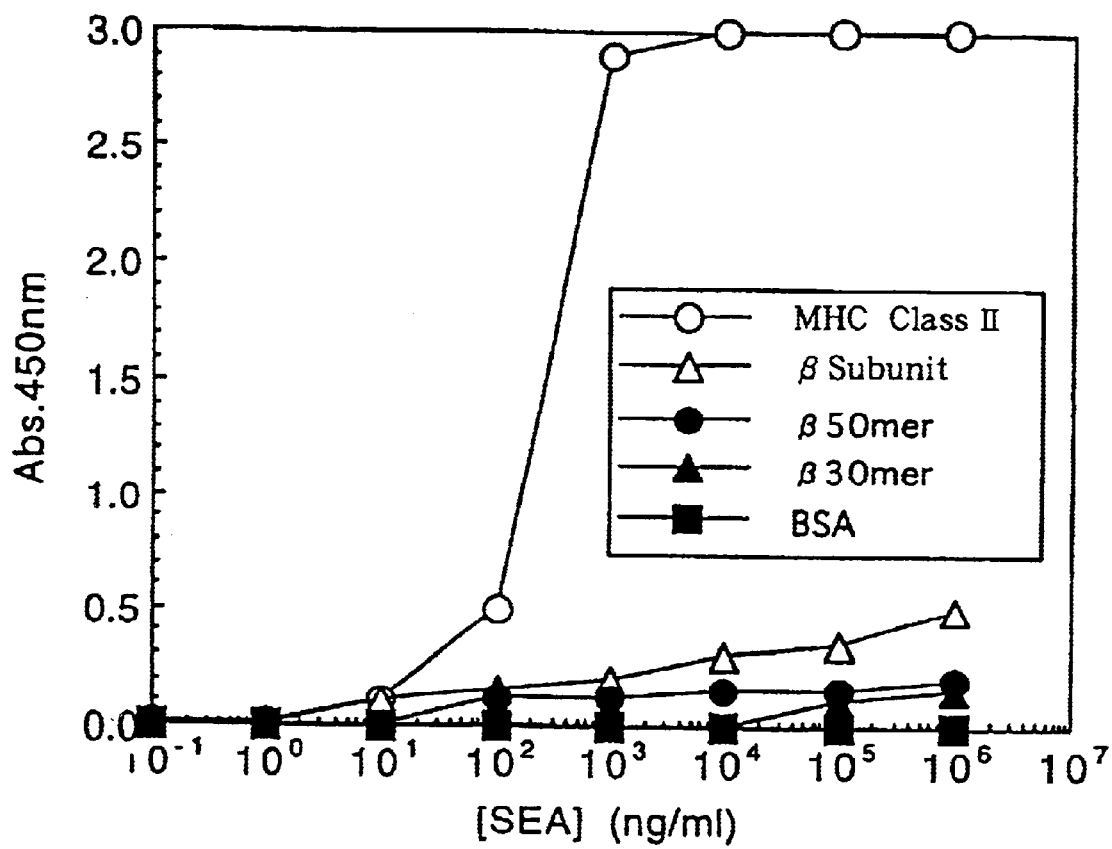
FIG. 5 shows the relationship between the SEA level and the absorbance at 450 nm in enzyme immunoassay (sandwich method) employing a plate to which MHC class II, β subunit of MHC class II or a partial sequence of β subunit of MHC class II is bound.

The gene encoding MHC class II used in the present invention was obtained by synthesizing DNA primers for PCR based on the reported DNA sequence (L. J. Stern et al., Cell, Vol. 68, p.465, (1992), D. A. Wettstein et al., J. Exp. Med. Vol. 174, p219, (1991)); and amplifying the gene in human cells such as B cells by conventional PCR method described in, for example, "PCR Method for Gene Amplification" (PROTEINS, NUCLEIC ACIDS AND ENZYMES, additional edition, Vol. 35, No. 17 (1990)). The protein encoded by the gene may be obtained by expressing the gene in *E. coli* cells, yeast cells, insect cells or mammalian cells according to a genetic recombination technique.

Among the cells just mentioned above, in view of the growth rate, production efficiency and ease of operations such as culturing, it is preferred to employ *E. coli* cells, yeast cells and *B. subtilis* cells. The protein may be expressed by ligating the gene with one of various known expression vectors after adding to the gene or a fragment thereto an initiation codon, a termination codon, and if it is desired to secrete the protein outside the cells, a sequence for secretion, and by expressing the gene or the fragment thereof directly. Alternatively, the protein or a fragment thereof may be expressed in the form of a fused protein with another peptide, such as interleukin 2, maltose-binding protein, β-galactosidase, trpE or the like. Further, in view of ease of purification of the protein after expression, hexamer of histidine or the like may be added as long as the activity of MHC class II is retained.

In view of the toxicity of MHC class II to the bacteria, it is preferred to form inclusion body in the form of a fused protein when the gene is expressed, or to employ a promoter having a high ability to control initiation of transcription, such as T7 ribonuclease promoter or heat shock promoter. It is also possible to introduce a recognition site of a protease (e.g., activated blood coagulation factor X (Factor Xa) and IgA protease) or a cleavage site by a chemical reagent (e.g., cyanogen bromide) between MHC class II and the other protein fused with MHC class II. By so doing, MHC class II may be separated from the other protein after expression of the gene. After expression, MHC class II may be purified by known methods including precipitation by ammonium sulfate, ion-exchange chromatography, affinity chromatography, gel permeation chromatography and hydrophobic chromatography. Further, the method described in METHOD IN ENZYMOLOGY (Academic Press, 1980) may also be applied. The disulfide bond of the subunits may be corrected by adding protein disulfide isomerase, thioredoxin, prothionine, glutathione, β mercaptoethanol or the like.

To reconstitute MHC class II after expressing α subunit and β subunit separately, equimolar of the subunits are mixed and the mixture is left to stand at 4–60° C., preferably 20–40° C. for not less than 5 minutes, preferably not less than 60 minutes.

When mixing the subunits, a small amount of a denaturating agent (e.g., 1 M urea, 10% acetonitrile and the like) may be added, and the reconstitution may be accomplished while dialyzing the mixture within the above-mentioned temperature range.

The material according to the present invention to which MHC class II is bound may be obtained by binding the naturally occurring MHC class II or α and/or β subunit thereof or a part thereof obtained from cell membranes, or recombinant MHC class II obtained from transformed cells or bacteria, or α and/or β subunit thereof or a part thereof to a carrier such as beads, fibers, hollow fibers, textile, plate or tube via covalent bond.

It is preferred to use a recombinant MHC class II, especially one produced by *E. coli* or a yeast is preferred since large amount of MHC class II can be obtained efficiently.

Thus, the present inventors studied expression and binding of MHC class II, as well as the carrier, to succeed in developing a material to which MHC class II is bound without losing its activity. The details will now be described.

(1) MHC Class II

As the MHC class II, naturally occurring MHC class II isolated from antigen-presenting cells such as B cells and monocytes with or without stimulating the cells with γ-interferon or the like may be employed. Alternatively, recombinant MHC class II purified from MHC class II-producing cells obtained by transforming mammalian cells such as CHO cells and L cells or insect cells may be employed. It is preferred to employ a recombinant MHC class II, especially one produced by *E. coli*, a yeast or *B. subtilis*, because a large amount of the protein can be obtained efficiently. Even if a subunit of MHC class II or a part thereof is bound to a carrier, the material has a binding ability. However, in view of the strength of the binding, it is preferred that the part of MHC class II to be bound to the carrier preferably has not less than 40 amino acid residues. More preferably, α,β complex is employed.

(2) Method for Immobilization

MHC class II may be immobilized by utilizing covalent bond, ionic bond, coordinate bond or hydrophobic bond, or by inclusion method or by adsorption. To prevent liberation of the immobilized protein, binding the protein via covalent bond is best preferred.

When binding a protein to a carrier, amino group, carboxylic group or sulfide group of the protein is usually utilized. In view of the fact that the binding site to superantigens is located in the N-terminal region of MHC class II, it is preferred to utilize carboxylic group for binding the protein.

(4) Carrier for Immobilizing Protein

As the carrier on which MHC class II is immobilized, beads, fibers, hollow fibers, plates and tubes made of synthetic polymers such as polymethylmethacrylates, polystyrenes, polysulfones, polyallylamines, polyvinylalcohols and derivatives thereof; naturally occurring polymers such as cellulose, chitosan and derivatives thereof; and inorganic materials such as ceramics and metals may be employed. Among these, polymeric compounds in which a functional group can easily be inserted are preferred as the material for binding MHC class II. In view of the ease of operation and large surface area, the carrier is preferably in the form of hollow fibers, beads, fibers and textiles.

By studying the binding method of MHC class II to a carrier, by which the activity of MHC class II can be utilized at maximum, the present inventors succeeded in providing a module for purifying blood by which superantigens are specifically captured.

Further, in a method for detecting or quantifying superantigens, by using MHC class II, α subunit of MHC class II, β subunit of MHC class II or a part thereof, it was attained for capturing all superantigens by using one material in which the protein or a part thereof is immobilized.

Since the binding ability to superantigens is influenced by three-dimensional structure of the protein, in order to firmly binding superantigens, the part of the protein has amino acid residues of not less than 30, preferably not less than 40. To immobilize the whole subunit is more preferred and binding MHC class II constituted from α and β subunits are best preferred.

The invention will now be described by way of examples thereof. It should be noted, however, the present invention is not restricted to the examples.

EXAMPLES

Example 1
Expression of MHC Class II α Subunit in E. Coli

The α subunit of MHC class II was prepared as follows:

Between the Eco RI site and Xba I site of pUEF having a heat shock promoter, a sequence encoding β galactosidase and a sequence encoding the recognition site of activated blood coagulation factor, Factor Xa, the gene encoding α subunit of MHC class II was inserted (FIG. 1). E. coli was transformed with this vector. After culturing the E. coli cells at 30° C. for 8 hours, the temperature of the culture medium was raised to 42° C. and kept at this temperature for 15 minutes to induce the production of the protein. Thereafter, the temperature of the culture medium was lowered to 37° C. and the cells were cultured at this temperature for 2 hours. The E. coli cells were then harvested.

Since MHC class II is produced in the form of a protein fused with β galactosidase, the fused protein can be purified by using a column to which p-aminophenyl-1-thio-β-D-galactopyranoside is fixed. Further, since the fused protein has a recognition site of Factor Xa between β galactosidase and MHC class II, α subunit of MHC class II which does not contain the protective protein β galactosidase can be obtained by digesting the fused protein with Factor Xa after expressing the fused protein.

Example 2
Expression of β Subunit of MHC Class II in the Form of Insoluble Protein β subunit of MHC class II was prepared as follows:

The gene encoding β subunit of MHC class II was inserted between Eco RI site and Hind III site of pTI vector having tryptophan promoter, a sequence encoding trpE protein and a sequence encoding the recognition site of IgA protease (FIG. 2). E. coli was transformed with this vector. After culturing the E. coli cells at 37° C. for 8 hours in M9 medium, indole acrylic acid was added to induce the production of the protein. The cells were further cultured for 2 hours after the induction and E. coli cells were harvested from the culture medium.

Since β subunit of MHC class II is produced in the form of a fused protein with trpE protein, the desired protein is precipitated in the insoluble fraction. After washing the insoluble fraction with Tris buffer containing 2 M urea, the desired fused protein was solubilized by using Tris buffer containing 8 M urea. When the fused protein is solubilized, by adding 1 mM dithiothreitol or 2% β mercaptoethanol as a reducing agent, the recovery of the fused protein is promoted. Immediately after the solubilization, fractionation based on molecular weight is performed by gel permeation chromatography so as to separate the desired fused protein from contaminating lipids and other highly insoluble proteins. Thereafter, the fraction containing the desired fused protein is dialyzed in 20 mM Tris-HCl buffer (pH 7.4) including 50 mM sodium chloride buffer. After the dialysis, no precipitate is formed so that 100% of the fused protein can be recovered. Although the desired protein is obtained in the soluble fraction without the above-mentioned fractionation according to molecular weight, most part of the obtained protein is precipitated in the insoluble fraction after dialysis.

β subunit of MHC class II which does not contain trpE protein that is a protective protein can be obtained by digesting the obtained soluble fraction with IgA protease, and by purifying the β subunit by hydrophobic chromatography, ion-exchange chromatography, gel permeation chromatography or the like. The purification by hydrophobic chromatography or ion-exchange chromatography may be performed before the digestion by the protease.

Example 3
Reconstruction of MHC Class II from α and β Subunits

The α subunit and the β subunit of MHC class II prepared in Examples 1 and 2, respectively, are dissolved in Tris-HCl buffer (pH 7.4) containing 8 M urea, 10 mM magnesium chloride and 100 mM sodium chloride, to a concentration of 5 mg/ml each. Thereafter, the resulting solution is dialyzed in 10 mM magnesium chloride solution containing 1 M urea and in Tris-HCl buffer (pH 7.4) containing 100 mM sodium chloride at 4° C. After the dialysis, the resultant is further dialyzed in 10 mM magnesium chloride solution containing no urea and in Tris-HCl buffer (pH 7.4) containing 100 mM sodium chloride. By these operations, MHC class II complex can be obtained.

Example 4

MHC class II produced by E. coli was bound to beads. This was accomplished as follows: MHC class II was dissolved in 5 ml of 50 mM borate buffer (pH 8.0) to a concentration of 1 mg/ml. To this aqueous solution, 1 ml of chitosan beads having succinimide groups were added and the resulting mixture was allowed to react at 4° C. for 8 hours. After the reaction, inactivation of the non-reacted functional groups and washing of non-reacted protein were performed with 50 ml of 0.5 M Tris-HCl buffer (pH 8.0). Amino acid analysis of the obtained beads revealed that the amount of the protein bound to the beads was 2.3 mg per 1 ml of beads. In an aqueous solution containing exotoxin of *Staphylococcus aureus* (TSST-1) in a concentration of 1 ng/ml, 0.5 ml of the thus obtained MHC class II-bound beads were added. For comparison, 0.5 ml of chitosan beads having succinimide groups, which were reacted only with Tris-HCl buffer were also separately added to the TSST-1 solution. As shown in FIG. 3, adsorption of the toxin was observed only in the solution to which MHC class II-bound beads were added. Thus, it was confirmed that MHC class II was bound to the beads via covalent bond while retaining the binding ability to the toxin. In FIG. 3, ○ indicates the results of the test using MHC class II-bound beads and ● indicates the results of the test using non-reacted beads. Only with MHC class II-bound beads, the reduction of TSST-1 concentration was observed.

Example 5

MHC class II produced by *E. coli* was bound to hollow fiber membranes as follows: MHC class II was dissolved in 5 ml of 50 mM borate buffer (pH 8.0) to a concentration of 1 mg/ml. To the obtained aqueous solution, 1 g of polysulfone hollow fibers having amino groups were added and the mixture was allowed to react at 4° C. for 8 hours.

To the reaction mixture, carbodiimide was added as a catalyst. Amino acid analysis of the obtained hollow fibers revealed that 2.0 mg of protein was bound per 1 g of the hollow fibers. A module was prepared using 0.5 g of the thus obtained MHC class II-bound hollow fibers. For comparison, a module was also prepared using 0.5 g of hollow fibers which were not reacted with MHC class II. A serum containing exotoxin of *Staphylococcus aureus* (TSST-1) in a concentration of 1 ng/ml was circulated in each module. As a result, as shown in FIG. 4, adsorption of the toxin was observed only with MHC class II-bound hollow fibers. Thus, it was proved that removal of the toxin from blood can be attained by MHC class II-bound hollow fibers. In FIG. 4, ○ indicates the results of the test using MHC class II-bound hollow fibers and ● indicates the results of the test using non-reacted hollow fibers. Only with MHC class II-bound hollow fibers, the reduction of TSST-1 concentration was observed.

Example 6

MHC class II extracted from B cells, β subunit of MHC class II produced by *E. coli*, or a partial amino acid sequence of β subunit of MHC class II (30 amino acid residues which is said to have binding ability to superantigens) was dissolved in PBS to a concentration of 10 μg/ml. Each of the solutions was placed in an amount of 0.1 ml in the wells of a 96-well microplate having amino groups, and carbodiimide as a catalyst was added thereto. Each of the mixtures was left to stand overnight at 4° C. to immobilize the protein. After blocking the wells with PBS solution containing 0.5% bovine serum albumin (BSA), the wells were washed with a washing solution (PBS containing 0.05% Tween 20).

With the thus prepared MHC class II-bound plate, SEA which is exotoxin of *Staphylococcus aureus* and is a superantigen was reacted. As a control, SEA was reacted with a plate to which BSA alone was immobilized. Thereafter, anti-SEA monoclonal antibody (labelled with biotin), avidin-conjugated peroxidase, and 3,3',5,5'-tetramethylbenzidine were sequentially reacted, and the generated color was measured. The results are shown in FIG. 5. Coloring was scarcely observed in the plate to which BSA alone was immobilized. Coloring was observed in the plates to which MHC class II (about 400 amino acid residues), β subunit (about 200 amino acid residues), or the peptide having a partial amino acid sequence (50 amino acid residues or 30 amino acid residues) was bound, so that binding of SEA was confirmed. ○ indicates the results obtained with the MHC class II-bound plate, Δ indicates the results obtained with the β subunit-bound plate, ● indicates the results obtained with the partial amino acid sequence of β subunit-bound plate (50 amino acid residues), ▼ indicates the results obtained with the partial amino acid sequence of β subunit-bound plate (30 amino acid residues), and ■ indicates the results obtained in the control (BSA-immobilized plate).

With the increase in the number of amino acid residues, detection sensitivity is increased, and with an sequence having not less than 50 amino acid residues, SEA at a concentration of 1 μg/ml can be detected. With the MHC class II-bound plate and the β subunit of MHC class II-bound plate, the relationship between the coloring and SEA level is linear within the range of the SEA level from 0 to 1 μg/ml and from $10^3$ to $10^6$ ng/ml, respectively. Thus, it was proved that quantification of SEA can be attained.

INDUSTRIAL APPLICABILITY

By the present invention, major histocompatibility antigen class II protein which is hitherto produced by using mammalian cells or insect cells can be produced efficiently at a low cost in a large scale by using bacterial cells.

The present invention also provides a material which is useful for adsorbing, separating, detecting or quantifying superantigens or the like, such as exotoxin of *Staphylococcus aureus* in aqueous solutions, body fluids such as blood and urine, foods and drinks. Thus, the present invention may be effectively employed in studies in medicine, immunology and biochemistry as well as in clinical applications, for example, for constructing therapeutic systems for sepsis and autoimmune diseases.

What is claimed is:

1. A method for adsorbing superantigens comprising contacting said superantigens with a material having an immobilizing carrier and major histocompatibility antigen class II protein or a part thereof bound to said carrier via covalent bond.

2. A method for adsorbing superantigens comprising contacting said superantigens with a material having an immobilizing carrier and an α subunit of major histocompatibility antigen class II protein or a part thereof bound to said carrier via covalent bond.

3. A method for adsorbing superantigens comprising contacting said superantigens with a material having an immobilizing carrier and a β subunit of major histocompatibility antigen class II protein or a part thereof bound to said carrier via covalent bond.

4. The method according to any one of claims 1–3, wherein said immobilizing carrier is selected from the group consisting of hollow fiber membranes, fibers, beads, textiles, plates and tubes.

5. The method according to any one of claims 1–3, wherein said superantigens are adsorbed from blood.

* * * * *